United States Patent [19]

Van Rheenen

[11] 4,443,377

[45] Apr. 17, 1984

[54] ISOMERIZATION-ACYLATION PROCESS

[75] Inventor: Verlan H. Van Rheenen, Kalamazoo County, Mich.

[73] Assignee: The Upjohn Company, Kalamazoo, Mich.

[21] Appl. No.: 419,843

[22] Filed: Sep. 20, 1982

[51] Int. Cl.³ .............................................. C07J 5/06
[52] U.S. Cl. .............................. 260/397.4; 260/397.3
[58] Field of Search ...................................... 260/397.4

[56] References Cited

U.S. PATENT DOCUMENTS 3,359,287 12/1967 Babcock et al. ............... 260/397.4
3,705,181 12/1972 Parikh et al. .................... 260/397.4
4,154,748 5/1979 Van Rheenen ................. 260/397.4

*Primary Examiner*—Elbert L. Roberts
*Attorney, Agent, or Firm*—Bruce Stein

[57] ABSTRACT

17α-Hydroxy-6,16-dimethylenepregn-4-ene-3,20-dione simultaneously isomerized and acylated to 17α-hydroxy-6-methyl-16-methylenepregna-4,6-diene-3,20-dione 17-acetate.

5 Claims, No Drawings

ISOMERIZATION-ACYLATION PROCESS

BACKGROUND OF THE INVENTION

Melengestrol acetate (XI,17α-hydroxy-6-methyl-16-methylenepregna-4,6-diene-3,20-dione 17-acetate) is known to be useful as a progestation agent in the veterinary area. U.S. Pat. No. 3,359,287 (Example 4) discloses that melengestrol acetate is prepared by dehydrogenating 17α-hydroxy-6α-methyl-16-methylenepregn-4-ene-3,20-dione 17-acetate (XII) with chloranil.

U.S. Pat. No. 4,154,748 reports an alternative procedure for production of melengestrol acetate in which the last step is acetylation of 17α-hydroxy-6-methyl-16-methylene-pregna-4,6-diene-3,20-dione.

U.S. Pat. No. 3,705,181 discloses the simultaneous isomerization and 17-acylation of 17α-hydroxy-6-methylenepregn-4-ene-3,20-dione to 17α-hydroxy-6-methylpregna-4,6-diene-3,20-dione 17-acetate by reaction with acetic anhydride and p-TSA in benzene. It should be noted that the steroid of U.S. Pat. No. 3,705,181 did not contain any substitution at $C_{16}$ whereas the starting material of the present invention contains the reactive methylene group at $C_{16}$.

BRIEF DESCRIPTION OF THE INVENTION

The present invention is a process for the preparation of 17α-hydroxy-6-methyl-16-methylenepregna-4,6-diene-3,20-dione 17-acetate (XI) which comprises (1) contacting 17α-hydroxy-6,16-dimethylenepregn-4-ene-3,20-dione (X) with an acylating agent in the presence of a strong acid and (2) isolating the 17α-hydroxy-6-methyl-16-methylenepregna-4,6-diene-3,20-dione 17-acetate.

DETAILED DESCRIPTION OF THE INVENTION

The 17α-hydroxy-6,16-dimethylenepregn-4-ene-3,20-dione (X) starting material can be prepared by hydrolyzing 17α-hydroxy-6,16-dimethylenepregn-4-ene-3,20-dione 17-acetate (XIII, U.S. Pat. No. 3,117,966, Example 12). Alternatively it can be prepared by starting with androstenedione (I) in its $C_3$ protected form (1) adding the 16-methylene group, (2) ethynylating to produce the 17α-ethynyl-17β-hydroxy functionality, (3) adding the 6-methylene group and finally (4) transforming the 17α-ethynyl-17β-hydroxy functionality to the desired 17α-hydroxyprogesterone side chain as more fully described below.

The 16-methylene-17-keto steroid (III) is known to those skilled in the art. See, for example, Hungarian Pat. No. 019,495 and it can be readily prepared by methods well known to those skilled in the art from known compounds, see Gazz. Chim. Ital. 91, 672 (1961).

It is preferred that the 16-methylene-17-keto steroid (III) be prepared by conversion of androstenedione (I) to the 16-methylene-17-keto steroid (III) via a 16-substituted steroid intermediate (II), see Chart A. The process can be performed two different ways: (1) with isolation of the 16-substituted intermediate (II), and (2) without isolation of the 16-substituted intermediate (II). In the first case, the 17-keto steroid (I) is reacted with a $C_{16}$ activating agent in the presence of a strong base, the intermediate (II) is isolated and reacted with a formaldehyde generating agent in the presence of a base. In the second case, after the 16-substituted intermediate (II) is generated, the formaldehyde generating agent is added without additional base. These two processes are considered the equivalent of each other.

The 17-keto steroid (I), or as the $C_3$ protected form, is reacted with a $C_{16}$ activating agent in the presence of an enolizing base. The 17-keto steroid (I) can be protected at $C_3$ as the enol ether, ketal or enamine as is well known to those skilled in the art, see Chart D. It is preferred that the blocking group be the enol ether or ketal and the methyl, ethyl esters and ethylene ketal are most preferred. Chart A exemplifies the enol ester protecting group. The $C_{16}$ activating agent is a compound which when reacted with a 17-keto steroid (I) and an enolizing base activates the $C_{16}$ position of the 17-keto steroid (I) so as to make it reactive to the addition of formaldehyde. $C_{16}$ activating agents include compounds of the formula X—CO—R where R is a hydrogen atom or an electron withdrawing group such as a trifluoromethyl group, cyano group or $COOR_{16}$. The leaving group, X, is $OR_b$, or a chlorine, bromine or iodine atom. It is preferred that the $C_{16}$ activating group is selected from the group consisting of oxylal esters (such as methyl and ethyl oxylate), formyl esters (such as methyl or ethyl formate), trifluoroacetate esters (such as methyl or ethyl trifluoroacetate).

The enolizing base is a base sufficiently strong to form an enolate at $C_{17}$ and in conjunction with a $C_{16}$ activating agent form a 16-substituted intermediate (II). Generally the enolizing base is a strong base which has a pK of greater than 12. It is preferred that the enolizing base be selected from the group consisting of metal-$ORb$, metal hydride, or metal amides. Metal refers to lithium, sodium, potassium or magnesium, and Rb is alkyl of 1 thru 5 carbon atoms or phenyl. Enolizing bases include, for example, sodium methoxide, potassium ethoxide, sodium hydride, or lithium diisopropylamide. It is preferred that the metal is sodium and the base is sodium methoxide or sodium ethoxide. The reaction should be performed in an inert solvent, preferably selected from solvents such as toluene, methylene chloride, THF, but may also be performed in alcohols such as methanol, ethanol, etc. The reaction should be performed under an inert atmosphere, preferably nitrogen, in a temperature range of about $-20°$ to about $50°$.

The reaction is monitored by TLC as is well known to those skilled in the art. When the reaction is complete, the 16-substituted steroid (II) can be isolated or can be reacted in situ to produce the desired 16-methylene-17-keto steroid (III).

In either event, formaldehyde or a formaldehyde generating agent is then added. Before the formaldehyde generating agent is added, it is important to neutralize all the excess enolizing base. This is preferably done by the addition of an acid such as acetic acid or hydrochloric acid. A formaldehyde generating agent is a compound which, when used or reacted, acts as, or generates formaldehyde (HCHO) so that the formaldehyde generating agent could be formaldehyde itself or a compound or polymer which produces formaldehyde in situ or acts as formaldehyde. It is preferred that the formaldehyde generating agent be selected from the group consisting of formaldehyde, paraformaldehyde, trioxane and an aqueous or alcoholic solution of formaldehyde. It is more preferred that the formaldehyde generating agent be paraformaldehyde or an aqueous solution of formaldehyde. In the event that the 16-substituted steroid (II) is not isolated and the reaction is being performed as a one-pot process, the reaction mixture is sufficiently basic to cause the transformation of the 16-substituted steroid (II) to the 16-methylene-17-keto steroid (III). If the reaction is being performed as a two-pot process with isolation of the 16-substituted steroid (II) intermediate, the second step requires that a base be added. There may be a strong base such as $OR_b$ or a weak base such as tertiary amines. Preferred weak bases include, for example, triethylamine, tributylamine, or pyridine. Triethylamine is the preferred weak base. The reaction should be performed in an inert solvent such as the first step. The weak base can serve as solvent or cosolvent. The reaction is performed under an inert atmosphere, preferably nitrogen, in a temperature range of 0° to reflux. The reaction is monitored by TLC as is well known to those skilled in the art and is complete in 0.25 to 6 hr, usually about 1 hr, depending on temperature, etc. When complete, the 16-methylene steroid (III) is isolated and purified by means well known to those skilled in the art.

If the 16-methylene-17-keto steroid (III) is obtained in a $C_3$ protected form, the $C_3$ protecting group is readily removable and the A ring functionality is readily convertible to the unprotected form by means well known to those skilled in the art.

The 16-methylene-17-keto steroid (III) is converted to the corresponding 17α-ethynyl steroid (IV) by reaction with an appropriate reactive form of acetylene. In the present case the active acetylene agent, monolithium acetylide can be prepared by the process described by M. M. Midland in J. Org. Chem. 40, 2250 (1975). The $LiC_2H$ is prepared in a dry ether solvent such as THF, dioxane, diethyl ether, dimethyl ether at a temperature of less than $-20°$, preferably about $-20°$ to $-80°$, more preferably at about $-60°$. Alternatively and preferably the mono and lithium acetylide is generated in situ.

The 16-methylene-17-keto steroid (III) will have the functionality at $C_3$ protected during the ethynylation reaction as the enol ether, ketal, enamine or enol ester as is well known in the art. Chart A exemplifies the enol ether. $R_3$ is alkyl of 1 thru 5 carbon atoms, with the proviso that for the ketal the $R_3$'s can be connected. The preferred enol ether is the methyl or ethyl ether. The preferred ketal is the ethylene ketal. For the enamine $R_3'$ and $R_3''$ are alkyl of 1 thru 5 carbon atoms; $R_3'$ and $R_3''$ may be the same or different and the $R_3'$ and $R_3''$ can be connected. The preferred enamines are selected from the group consisting of pyrrolidine, morpholine and diethylamino amines. The enol ethers are prepared by methods well known in the art, see J. Org. Chem. 26, 3925 (1961), Steroid Reactions, Edited by Carl Djerassi, Holden-Day, San Francisco 1963, page 42–45, and U.S. Pat. No. 3,516,991 (Preparation 1). The ketals are also prepared by well known methods, see Steroid Reactions, supra, page 11–14. The 3-enamines are also prepared by methods well known in the art, see U.S. Pat. No. 3,629,298 and Steroid Reactions, supra, page 49–53.

The $C_3$ protected form of the $\Delta^4$-3-keto steroid is considered equivalent to the non-protected or free form since the $C_3$ protecting groups are readily removable to convert the $C_3$ protected forms to the free form.

The monolithium acetylide and the 16-methylene-17-keto steroid (III) are contacted slowly at a temperature of less than $-20°$, preferably about $-20°$ to $-70°$, more preferably at about $-60°$. At least 1.5 equivalents of monolithium acetylide are used. When the reaction is complete the excess acetylide is quenched or destroyed by reaction with a quenching agent which is any aqueous system such as water, saline or aqueous buffers depending on what final pH is desired. The preferred quenching agent is an aqueous buffer with a pH of about 7. The 17α-ethynyl steroid (IV) is obtained or isolated from the reaction mixture by means well known to those skilled in the art as the $C_3$ protected form. The $C_3$ protecting group is removed by means well known to those skilled in the art or the $C_3$ protecting group may be left on for further chemical modification of the 17α-ethynyl steroid (IV). Before the 17α-ethynyl steroid (IV) is isolated the $C_3$ protecting group can be hydrolyzed in situ so as to obtain the unprotected or free 17α-ethynyl steroid by reaction with an appropriate proton reagent depending on the nature of the $C_3$ protecting group as is well known to those skilled in the art. For example, if the 16-methylene-17-keto steroid (III) is protected as the enol ether the protecting group can be removed by acid so that the 17α-ethynyl steroid (IV) will be isolated in the free $\Delta^4$-3-keto form. Alternatively and preferably the monolithium acetylide is generated in situ. Operationally, this is much easier, and the reaction may be performed at about $-40°$ rather than at $-60°$ when the reagent is prepared separately. Using the in situ method an alkali metal amide base such as lithium diethylamide or diisopropylamide or an equivalent base is prepared by reacting the appropriate amine with an organolithium reagent such as n-butyl lithium or phenyl lithium. An acetylene saturated solution is added to an ether solvent (THF, diethyl ether, dioxane) containing the appropriate form of the 16-methylene-17-keto steroid (III) at about $-20°$. The lithium amide is then added to the mixture of the 16-methylene-17-keto steroid (III) and acetylene in the ether solvent. The reaction is stirred at about $-20°$ until complete as measured by TLC usually 0.5–2 hr. The reaction mixture is slowly added to a saline/water (1/1) mixture and then worked up in the usual manner.

The 17α-ethynyl steroid (IV) is then transformed to the corresponding 17α-ethynyl-6-methylene steroid (VI) by the process of U.S. Pat. No. 3,642,840. The 17α-ethynyl-6-methylene steroid (VI) is then transformed to the corresponding 17α-hydroxy steroid (VII) by reaction with a mercuric agent. Oxymercuration of ethisterone derivatives is well known, see Helv. Chim. Acta. 26, 680 (1943).

The mercuric agent can be produced by reaction of mercuric oxide with a strong acid such as sulfuric, hydrochloric, or nitric acid. The mercuric salts, mercuric sulfate, mercuric chloride or mercuric nitrate can be used directly in acid medium. Mercuric sulfate or this salt made from mercuric oxide and sulfuric acid is preferred. A catalytic amount of a mercuric agent and the 17α-ethynyl-6-methylene steroid (VI) are contacted at 20°–65° for 2–24 hr in an aqueous polar solvent. When the oxymercuration reaction is complete, the reaction mixture is filtered (thru Celite) to remove insoluble mercuric salt solids and the 17β-hydroxy steroid (VII) is recovered from the filtrate by means well known to those skilled in the art. Alternatively the oxymercuration reaction can be performed using the mercuric agent affixed to a resin. See M. S. Newman, J. Am. Chem. Soc., 75, 4740 (1953).

The 17β-hydroxy steroid (VII) is next converted to the corresponding sulfoxide (IX) by reaction with a sulfenylating agent of the formula $R_{22}$-S-M (VIII). It is preferred that M chlorine or bromine atom, more preferred that M be a chlorine atom. It is preferred that $R_{22}$ be methyl, phenyl, p-chlorophenyl, p-methoxyphenyl or p-methylphenyl. It is more preferred that $R_{22}$ be phenyl.

The appropriately substituted sulfenylating agents (VIII) are prepared by methods known to those skilled in the art. For example, sulfuryl chloride is added to a thiol previously dissolved in an organic solvent such as carbon tetrachloride. See Chem. Reviews, 39, 269 (1946) at page 279 and U.S. Pat. Nos. 2,929,820 and 4,041,055.

The sulfenylation reaction is carried out in a non-polar aprotic solvents such as toluene, chloroform, diethyl ether, or methylene chloride, THF, and dioxane or mixtures thereof. It is preferred that the solvent be methylene chloride. The reaction is carried out in the presence of at least an equal molar amount of a tertiary amine base, such as triethylamine, trimethylamine or pyridine. Trimethylamine is preferred. Any excess base serves as additional solvent for the reaction. The reaction is preferably carried out under an inert dry gas such as nitrogen, argon, or carbon dioxide. The sulfenyl halide (VIII) is added dropwise to the reaction mixture at a temperature of $-20°$ to $-40°$. Following addition of the sulfenylating agent (VIII) to the reaction mixture, the excess sulfenylating agent is quenched with an appropriate quenching agent such as water, cyclohexane, various alcohols such as methanol and ethanol, or acetone. The sulfoxide (IX) may be obtained by standard work-up.

The sulfoxide (IX) exists as 2 double bond isomers; the compound of formula (IX) and where the unsaturation is between $C_{16}$ and the carbon atom attached to the sulfur atom. The endocyclic isomer (IX) greatly predominates with only trace amounts of the exocyclic isomer. However, the ratio of the isomeric sulfoxides is unimportant for the purposes of the present invention as both isomers are converted to the same product in the next step.

The sulfoxide (IX) is converted to the corresponding 16-methylene-17α-hydroxyprogesterone (X) by reaction with a thiophile with heat. The sulfoxide (IX) is placed in an appropriate solvent or mixture of solvents such as toluene, methanol, ethylene dichloride or acetone. Some thiophiles such as hydroxide, alkoxide, etc. produce undesirable side reactions; others such as trimethylphosphite and diethylamine and mixtures thereof are more suitable. The preferred thiophile is trimethylphosphite. Trimethylphosphite is known as a thiophile, see D. A. Evans & G. C. Andrews, Acct. of Chem. Res. 7, 147 (1974) at p. 150. The sulfoxide (IX) and thiophile are contacted and heated from about 50°–100° depending on solvent(s), sulfoxide (IX), thiophile, and whether or not the reaction is conducted under pressure. It is preferred to heat the reaction mixture from 60°–90° in a sealed reacting container for 4–24 hr. When the reaction is complete the 16-methylene-17α-hydroxyprogesterone (X) is isolated and purified by means well known to those skilled in the art.

The 17α-hydroxy-6,16-dimethylenepregn-4-ene-3,20-dione (X) is reacted with an acetylating agent in the presence of a strong acid. The acetylation agent is selected from the group consisting of acetic anhydride, acetyl halide (preferably acetyl chloride), or an equivalent actylating agent such as isopropyl acetate. The preferred acetylating agent is acetic anhydride. The strong acid is selected from the group consisting of p-TSA, benzenesulfonic acid, methanesulfonic acid, p-nitrobenzenesulfonic acid, perchloric acid, sulfuric acid, phosphoric acid, hydrochloric acid and other acids which are substantially dissociated in non-aqueous systems are deemed equivalent. Preferred is p-TSA. The strong acid can be present in catalytic amounts (0.001 equivalents) or up to 10 equivalents, preferred is from about 0.05 to about 0.5 equivalents. The reaction can be performed in a temperature range of from about 20° to the reflux temperature of the reaction medium used, 50°–85° is preferred giving a reaction time of 2–10 hr. Suitable solvents for a reaction medium include benzene, toluene, xylene, cyclohexane, pentane, ethylene dichloride and chloroform and mixture thereof.

Following completion of the reaction the 17α-hydroxy-6-methyl-16-methylenepregna-4,6-diene-3,20-dione 17-acetate (XI) is recovered by means well known to those skilled in the art. The melengestrol acetate can be further purified by recrystallization from methanol or isopropanol.

DEFINITIONS

The definitions and explanations below are for the terms as used throughout the entire patent application including both the specification and claims.

All temperatures are in degrees Centigrade.

TLC refers to thin-layer chromatography.

THF refers to tetrahydrofuran.

Saline refers to an aqueous saturated sodium chloride solution.

p-TSA refers to p-toluenesulfonic acid.

NMR refers to nuclear (proton) magnetic resonance spectroscopy, chemical shifts are reported in ppm ($\delta$) downfield from TMS.

TMS refers to tetramethylsilane.

TEA refers to triethylamine.

When solvent pairs are used, the ratio of solvents used are volume/volume (v/v).

Androstenedione refers to androst-4-ene-3,17-dione.

M is a chlorine or bromine atom or phenylsulfone, phthalimide or imidazole group.

R is a hydrogen atom, trifluoromethyl or cyano group or $COOR_{16}$.

$R_3$ is alkyl of 1 thru 5 carbon atoms with the proviso that with the ketal, the $R_3$ groups can be connected.

$R_3'$ is alkyl of 1 thru 5 carbon atoms.

$R_3''$ is alkyl of 1 thru 5 carbon atoms.

$R_6$ is a hydrogen or fluorine atom, methyl or methylene group. When $R_6$ is methylene, there are no 6–7 double bonds in formula (A) or 5–6 double bonds in formula (C).

$R_9$ is nothing or a hydrogen or fluorine atom, which includes the $\Delta^{9(11)}$ and 9β,11β-epoxide functionality.

$R_{10}$ is a hydrogen atom or methyl group.

$R_{11}$ is nothing or a hydrogen or oxygen atom, an α-hydroxy group, or a β-hydroxy group, which includes the $\Delta^{9(11)}$ and 9β,11β-epoxide functionality.

$R_{16}$ is alkyl of 1 thru 3 carbon atoms.

$R_{22}$ is alkyl of 1 thru 5 carbon atoms, trichloromethyl, phenyl, phenyl substituted with 1 thru 4 carbon atoms or substituted with 1 thru 3 nitro or trifluoromethyl groups, aralkyl of 7 thru 12 carbon atoms, or $-N-(R_{122})_2$.

$R_{122}$ is alkyl of 1 thru 4 carbon atoms, phenyl or phthalimide.

. . . is a single or double bond.

∼ indicates that the attached group can be either the α or β configuration.

Metal refers to lithium, sodium, potassium or magnesium.

When the term "alkyl of ——— thru ——— carbon atoms" is used, it means and includes isomers thereof where such exist and are operable.

X is $OR_b$, or a chlorine, bromine, or iodine atom.

$R_b$ is alkyl of 1 thru 5 carbon atoms or phenyl.

A formaldehyde generating agent is a compound which, when used or reacted, acts as, or generates, formaldehyde (HCHO) so that the formaldehyde generating agent could be formaldehyde itself or a compound which produces formaldehyde in situ or acts as formaldehyde.

$C_{16}$ activating agent is a compound which, when reacted with a 17-keto steroid (I) and an enolizing base produces a 16-substituted intermediate (II) and activates the $C_{16}$ position of the 17-keto steroid (I) so as to make it reactive to the addition of formaldehyde.

An enolizing base is a base which when reacted with a 17-keto steroid (I) and a $C_{16}$ activating agent produces a 16-substituted intermediate (II).

Androstenedione refers to androst-4-ene-3,17-dione.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants as well as reaction conditions and techniques.

PREPARATION

3-Methoxy-16-methyleneandrosta-3,5-dien-17-one (III)

3-Methoxyandrosta-3,5-dien-17-one (I, 50.0 g) was dissolved in THF containing TEA (1 ml). Dimethyloxalate (55.5 ml) was added and the mixture cooled to 2°. Sodium methoxide (25%) in methanol (45.7 ml) was added slowly over 10 minutes. The ice bath was removed and the reaction warmed to 24° over five minutes with stirring. The mixture was stirred at 20°-25° for 55 minutes, then cooled to 5° over 10 minutes. Acetic acid (2.4 ml) was added, immediately followed by TEA (17.4 ml), then paraformaldehyde (7.49 g), followed by methanol (63 ml). The ice bath was removed and the mixture warmed to 20°-25° over 5 minutes. The mixture was stirred at 28° for 5 hrs and stored in a freezer (−20°) overnight. The mixture was then warmed to 20°-25° and stirred at 25° for 4 hrs for a total time of approximately 9.0 hrs at 20°-28°. Water (300 ml) and ethyl acetate (300 ml) were added, the mixture stirred and the layers separated. The organic layer was washed with saline (2×100 ml). The aqueous portion is backextracted with ethyl acetate (2×100 ml, washing each with 50 ml of saline). The organic phases are combined, concentrated under reduced pressure to an oil, taken up in methylene chloride (450 ml) and ethyl acetate (200 ml). This mixture was dried over sodium sulfate, filtered and concentrated under reduced pressure to a solid. Trituration of the solid with boiling methanol (100 ml) containing 1% TEA gives the title compound in crystalline form.

PREPARATION 2

17α-Ethinyl-17β-hydroxy-3-methoxy-16-methyleneandrosta-3,5-diene (IV)

Acetylene was bubbled through THF (450 ml) for 45 min at 20°-25°. The mixture was cooled to −70° over 15 min while acetylene saturation was continued. N-butyllithium (1.6 M, 150 ml) was added dropwise over about 45 min, maintaining the temperature at ≦−68°. The mixture was then warmed to −35° over 30 min. 3-Methoxy-16-methyleneandrosta-3,5-dien-17-one (III, Preparation 1, 30 g) in THF (150 ml) was added dropwise over 15 min, maintaining the temperature at about −25°. The mixture was stirred for 10 min; then the solution was added slowly to phosphate buffer (1 N, 800 ml) plus ice water (300 ml) at 0°. The transfer took approximately 1 hr, following which the mixture was stirred. Ethyl acetate (500 ml) was added and the layers separated. The ethyl acetate layer was washed with saline (2×300 ml). The aqueous phase was back-extracted with ethyl acetate (2×300 ml). The ethyl acetate back extracts were combined and washed once with saline (200 ml). The organic phases were combined, dried over anhydrous sodiumسulfate, filtered and concentrated under reduced pressure to a solid. The solid was triturated with hot methanol (100 ml) for 10 min, cooled to 20°-25°, then cooled to −20° for 2 hrs. The mixture was filtered, the crystals washed with cold methanol containing TEA, and dried under reduced pressure to give the title compound.

PREPARATION 3

17α-Ethinyl-17β-hydroxy-6β-(N-phenyl-N-ethylaminomethyl)-16-methyleneandrosta-4-en-3-one (V)

17α-Ethinyl-17β-hydroxy-3-methoxy-16-methyleneandrosta-3,5-diene (IV, Preparation 2, 5 g), ethyl aniline (2.05 ml), THF (37.5 ml), and formaldehyde (37%, 1.33 g) were mixed. p-TSA (140 mg) was added and the mixture stirred overnight at 20°-25°. TLC showed the reaction to be complete. Water (100 ml) was added, the mixture filtered, the solids washed twice with water/THF; 2/1, the solid material was dried under nitrogen for 5 hours to give the title compound. NMR (CDCl$_3$) 0.85, 1.31, 2.52, 5.23, 5.82, 6.7 and 7.2 δ.

PREPARATION 4

17α-Ethinyl-17β-hydroxy-6,16-dimethyleneandrosta-4-en-3-one (VI)

17α-Ethinyl-17β-hydroxy-6β-(N-phenyl-N-ethylaminomethyl)-16-methyleneandrosta-4-en-3-one (V, Preparation 3) in THF (20 ml) are mixed. Degassed hydrochloric acid (6 N, 55 ml plus 20 ml THF) are added. The mixture is stirred overnight at 20°-25° under nitrogen, at which time TLC shows the reaction to be complete. Water (110 ml) is added, the mixture filtered, the solids washed with 10% hydrochloric acid, twice with water, once with 5% sodium bicarbonate, and three times with water to neutrality. Solids were then dried under nitrogen overnight to give the title compound.

PREPARATION 5

17α-Acetyl-17β-hydroxy-6,16-dimethyleneandrosta-4-en-3-one (VII)

Mercuric oxide red (0.32 g) was mixed with sulfuric acid/water (sulfuric acid, 0.4 ml; water, 6.0 ml) and let stand overnight. 17α-Ethinyl-17β-hydroxy-6,16-dimethyleneandrosta-4-en-3-one (VI, Preparation 4, 5.0 g) is mixed with THF (15 ml). The mercuric sulfate solution is added and the reaction heated to 41°–49° over a period of 6 hrs at which time TLC indicates the reaction is completed. Sodium carbonate (0.79 g) in water (10 ml) is added and the mixture stirred for 5 min. Celite (5 g) is added and the mixture stirred ½ hr at 20°–25°. The mixture is filtered through Celite (5 g), the solids washed with methanol/THF; 1/1 (2×10 ml) and once with THF (10 ml), followed by methylene chloride (10 ml). The filtrate and washings are concentrated under reduced pressure to about 35 ml, at which point crystals begin forming. Methanol (50 ml) is added and the mixture again concentrated under reduced pressure and permitted to sit overnight at 20°–25° under nitrogen atmosphere. Water (500 ml) is added, slowly at first, with stirring over a period of 15 min. The mixture is filtered, the solids washed with water (3×20 ml), and hexane (2×10 ml). The solids were dried under nitrogen to give the title compound.

PREPARATION 6

6-Methylene-16-(phenylsulfinylmethyl)pregna-4,16-diene-3,20-dione (IX)

17α-Acetyl-17β-hydroxy-6,16-dimethyleneandrosta-4-en-3-one (VII, Preparation 5, 8.0 g) is dissolved in methylene chloride (66 ml) and cooled to −20°. Trimethylamine (2.56 ml) at −20° and methylene chloride (5 ml) are mixed and the trimethylamine mixture transferred by syringe to the steroid solution. To the cold steroid solution was added phenylsulfonylchloride (1.0 equivalence) by a syringe pump over 1 hr. TLC shows the reaction approximately 80–85% complete. Phenylsulfonylchloride (0.25 equivalence) was added over approximately 10 min, TLC showing the reaction to be approximately 95% complete. Phenylsulfonylchloride (0.10 equivalence) was then added for a total of 1.35 equivalence, at which time TLC shows the reaction to be complete. Hydrochloric acid (10%, 40 ml) was added all at once, the temperature now being 7°, and the mixture stirred for about 10 min. The phases are separated. The aqueus portion is back extracted with methylene chloride (10 ml). The organic extracts are washed with phosphate buffer (25 ml) and back extracted with methylene chloride (10 ml). The organic extracts are combined, dried over sodium sulfate overnight at 20°–25°. This mixture is filtered and the filtrate concentrated under reduced pressure to an oil, which is the title compound.

PREPARATION 7

17α-Hydroxy-6,16-dimethylenepregna-4-ene-3,20-dione (X)

6-Methylene-16-phenylsulfonylmethylpregna-4,16-diene-3,20-dione (IX, Preparation 6, 2.0 g) is placed in a 30-ml vial under nitrogen. Toluene (20 ml), methanol (2.89 ml), TEA (0.181 ml) and trimethylphosphite 1.02 ml) are added. After 1 hr at 20°–25°, the sealed vial was plunged into a hot oil bath with a bath temperature of 90° which is stirred at 90° for 4 hrs, at which time TLC shows the reaction to be essentially complete. The reaction mixture is transferred to a separatory funnel and water (10 ml) is added. Ethyl acetate (10 ml) is added to the organic mixture, which is washed with water (2×10 ml). The aqueous portion is back extracted with toluene/ethyl acetate: 1/1. After the phases are separated, the organic phase is filtered through sodium sulfate and the filtrate is concentrated under reduced pressure to a volume of about 8 ml. This concentrate is permitted to sit at 20°–25° for approximately ½ hr. The resulting crystals are washed down into a flask with toluene (2 ml) and cooled to 5° for 2 hrs, then to −20° for 48 hrs. The crystals were collected with toluene (−20°), then with hexane three times and dried under nitrogen to yield the title compound.

EXAMPLE 1

17α-Hydroxy-6-methyl-16-methylenepregna-4,6-diene-3,20-dione 17-acetate (XI)

17α-Hydroxy-6,16-dimethylenepregna-4-ene-3,20-dione (X, Preparation 7, 50 mg) is slurried in toluene (1.5 ml). Acetic anhydride (95 μl, 7 equivalents) and p-TSA.H₂O (8 mg, 0.3 equivalents) are added. The reaction vessel is capped and heated at 85° for 3 hrs 20 min, then pulled from the heat, cooled and TLC shows the reaction is approximately 70% complete. The reaction mixture is heated for an additional 3 hrs, permitted to stand at 20°–25° overnight, at which time TLC shows the reaction is complete. Hydrochloric acid (6 N, 200 μl) is added and the mixture stirred 1 hr at 20°–25°. On work-up, the title compound is obtained

EXAMPLE 2

17α-Hydroxy-6-methyl-16-methylenepregna-4,6-diene-3,20-dione 17-acetate (XI)

17α-Hydroxy-6,16-dimethylenepregn-4-ene-3,20-dione (X, Preparation 7, 0.5 g) was slurried in toluene (14 ml) under a nitrogen atmosphere. Acetic anhydride (0.95 ml) was added followed by p-TSA (80 mg). The mixture is heated in a sealed vial at 85° for 6.5 hr at which time TLC indicated the reaction was complete. The mixture was concentrated under reduced pressure to an oil. Methanol (about 10 ml) was added followed by hydrochloric acid (10%, 1.5 ml) and the mixture stirred under nitrogen for 1 hr. Water was added, the mixture filtered. The solid was washed with bicarbonate, distilled water and dried overnight under nitrogen to give the title compound. (515 mg, 92% chemical yield).

CHART A

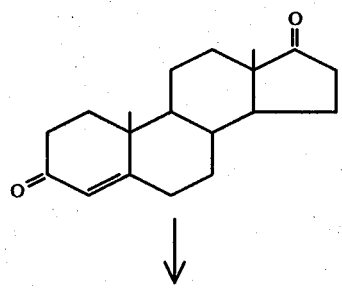

(I)

-continued
CHART A
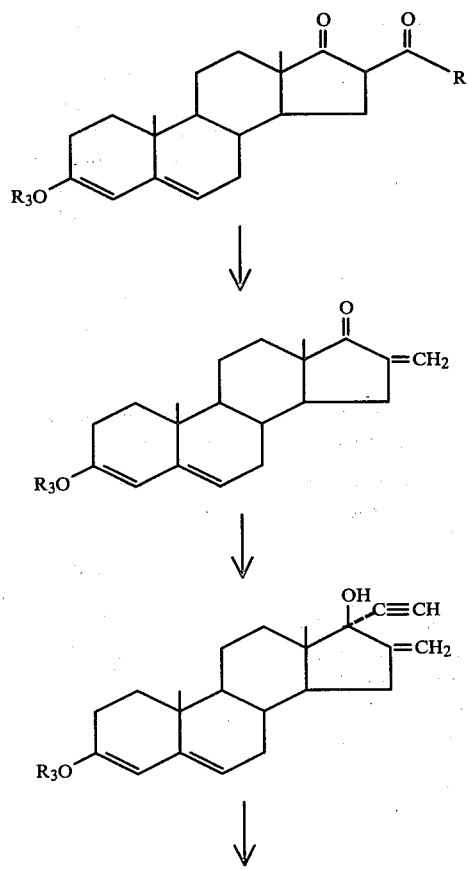
-continued
CHART B
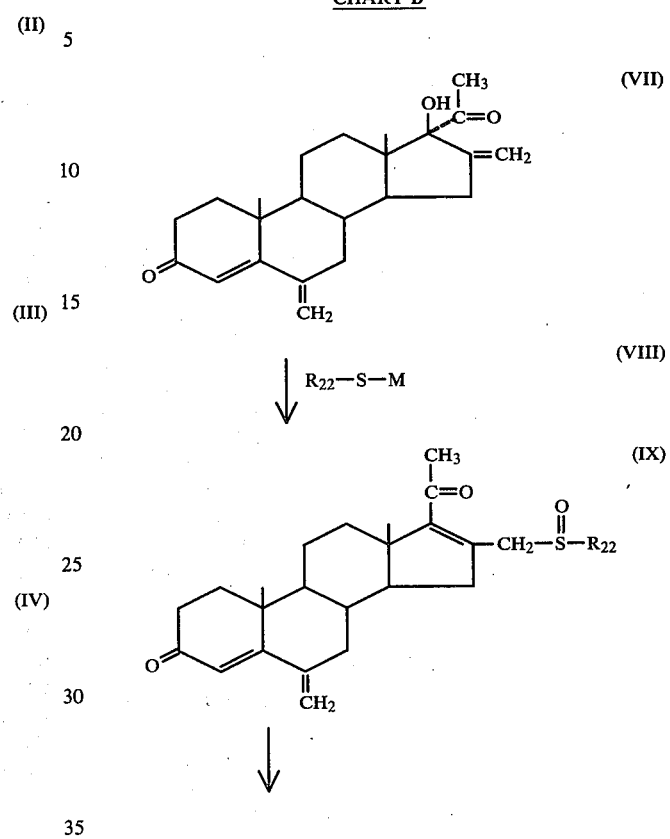
CHART C
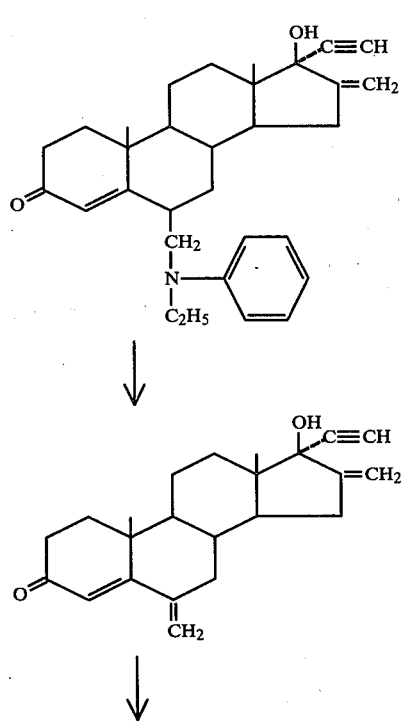
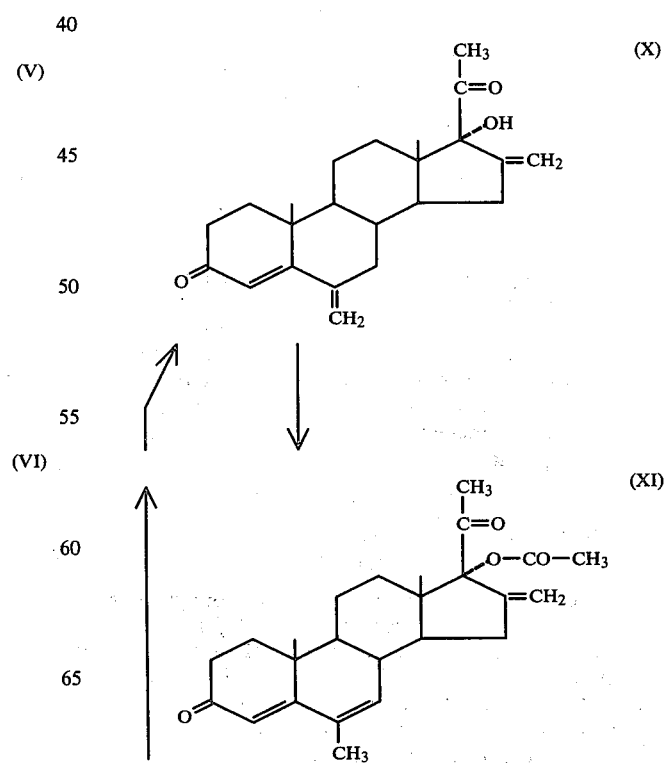

-continued
CHART C

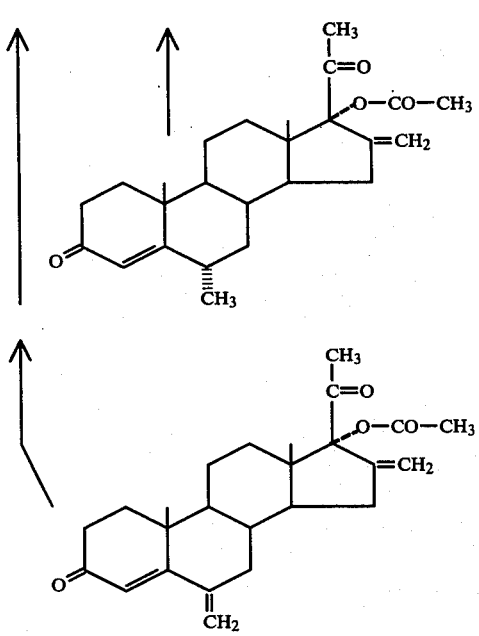

CHART D

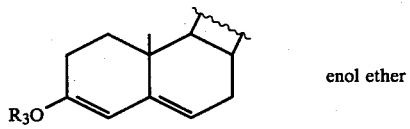
enol ether

-continued
CHART D

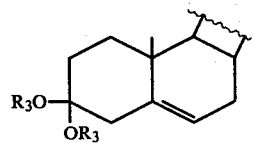
ketal

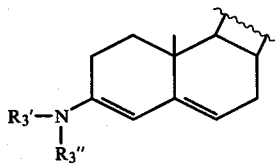
enamine

I claim:
1. A process for the preparation of 17α-hydroxy-6-methyl-16-methylenepregna-4,6-diene-3,20-dione 17-acetate which comprises
   (1) contacting 17α-hydroxy-6,16-dimethylenepregn-4-ene-3,20-dione with an acetylating agent in the presence of a strong acid and
   (2) recovering the 17α-hydroxy-6-methyl-16-methylenepregna-4,6-diene-3,20-dione 17-acetate.
2. A process according to claim 1 where the acetylating agent is selected form the group consisting of acetic anhydride, acetyl halide and isopropenyl acetate.
3. A process according to claim 2 where the acetylating agent is acetic anhydride.
4. A process according to claim 1 where the strong acid is selected from the group consisting of p-TSA, sulfuric acid, hydrochlorid acid, phosphoric acid, benzenesulfonic, methansesulfonic, p-nitrobenzenesulfonic, perchloric and mixtures thereof.
5. A process according to claim 4 where the strong acid is p-TSA.

* * * * *